United States Patent
Smithgall (10) Patent No.: US 10,603,321 B2
(45) Date of Patent: Mar. 31, 2020

(54) SMALL MOLECULES TARGETING HIV-1 NEF

(71) Applicant: University of Pittsburgh - of the Commonwealth System of Higher Education, Pittsburgh, PA (US)

(72) Inventor: Thomas E. Smithgall, Wexford, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 15/897,776

(22) Filed: Feb. 15, 2018

(65) Prior Publication Data

US 2018/0169098 A1    Jun. 21, 2018

Related U.S. Application Data

(62) Division of application No. 15/042,069, filed on Feb. 11, 2016, now Pat. No. 9,925,190.

(60) Provisional application No. 62/116,861, filed on Feb. 16, 2015.

(51) Int. Cl.
| | | |
|---|---|---|
| A61K 31/513 | (2006.01) | |
| A61K 31/501 | (2006.01) | |
| A61K 45/06 | (2006.01) | |
| A61K 31/428 | (2006.01) | |
| A61K 31/4155 | (2006.01) | |

(52) U.S. Cl.
CPC ........ *A61K 31/513* (2013.01); *A61K 31/4155* (2013.01); *A61K 31/428* (2013.01); *A61K 31/501* (2013.01); *A61K 45/06* (2013.01)

(58) Field of Classification Search
CPC .................................................. A61K 31/513
See application file for complete search history.

(56) References Cited

U.S. PATENT DOCUMENTS

| | | | | |
|---|---|---|---|---|
| 5,620,997 A | * | 4/1997 | Bolton | C07D 275/04 514/373 |
| 7,101,676 B2 | * | 9/2006 | Buechter | C07K 14/005 424/184.1 |
| 8,541,415 B2 | | 9/2013 | Sedlak et al. | |
| 9,643,922 B2 | * | 5/2017 | Jorgensen | C07D 209/18 |
| 2006/0020012 A1 | | 1/2006 | Jones et al. | |

FOREIGN PATENT DOCUMENTS

| | | |
|---|---|---|
| WO | WO 02/30907 | 4/2002 |
| WO | WO 02/100853 | 12/2002 |
| WO | WO 2014/074628 | 5/2014 |

OTHER PUBLICATIONS

Turpin et al., (J'nal f Med. Chem. (1999), 42(1),67-86.*
Tummino et al., Antimicrobial Agents and Chemotherapy (1997), 41(2), 394-400.*
Furdas et al., Institute of Pharmaceutical Sciences, MedChemComm (2014), 5(12), 1856-1862.*
Betzi et al., "Protein protein interaction inhibition (2P2I) combining high throughput and virtual screening: Application to the HIV-1 Nef protein," *Proc. Natl. Acad. Sci.*, 104(49): 19256-19261, Dec. 4, 2007.
Chutiwitoonchai et al., "The identification of a small molecule compound that reduces HIV-1 Nef-mediated viral infectivity enhancement," *PLoS One*, 6(11): 12 pages, Nov. 2011.
Cichero et al., "Docking-based 3D-QSAR analyses of pyrazole derivatives as HIV-1 non-nucleoside reverse transcriptase inhibitors," *J. Mol. Model.*, vol. 18, pp. 1573-1582, Apr. 2012.
International Search Report and Written Opinion issued for International Application No. PCT/US2012/068791 dated Feb. 28, 2014.
Iyer et al., "Synthesis and Structure-activity Analysis of Diphenylpyrazolodiazene Inhibitors of the HIV-1 Nef Virulence Factor," *Bioorg. Med. Chem. Lett.*, 24(7): 1702-1706, Apr. 1, 2014.
Smithgall et al., "Small molecule inhibitors of the HIV-1 virulence factor, Nef," *Drug Discov. Today Technol.*, 10(4): e541-e548, Jul. 2013.
Trible et al., "Discovery of a diaminoquinooxaline benzenesulfonamide antagonist of HIV-1 Nef function using a yeast-based phenotypic screen," *Retrovirology*, 10(135): 1-17, Nov. 14, 2013.
U.S. Appl. No. 14/441,475, filed May 7, 2015.

* cited by examiner

*Primary Examiner* — Paul V Ward
(74) *Attorney, Agent, or Firm* — Klarquist Sparkman, LLP (57) ABSTRACT

A method of treating HIV in a subject, comprising administering to a subject in need thereof a therapeutically effective amount of a compound having a general Formula 1, or a pharmaceutically acceptable salt or ester thereof:

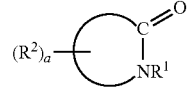

Formula 1 wherein $R^1$ is selected from H, optionally-substituted aryl, optionally-substituted heteroaryl, or optionally-substituted aliphatic; each $R^2$ is independently selected from H, halogen, cyano, thioether, oxo, optionally-substituted amino, optionally-substituted heteroaryl, optionally-substituted aryl, or optionally-substituted aliphatic; a is 3 to 7; and the ring designates a heterocyclic or heteroaryl structure.

11 Claims, 1 Drawing Sheet

| Compound | ID | MW | Nef + Hck IC$_{50}$, μM | Hck alone IC$_{50}$, μM | HIV Replication MDM, IC$_{50}$, μM | Toxicity MDM, TC$_{50}$, μM | Nef binding (SPR)[a] Kinetic Kd (M) | Nef binding (SPR)[a] Steady-state Kd (M) | Nef binding (SPR)[a] Two-state Kd (M) |
|---|---|---|---|---|---|---|---|---|---|
| | SRI-1261 | 287 | 0.8 | >100 | 0.04 | >100 | N/A[b] | 2.29×10⁻⁵ (global) | 3.14×10⁻⁵ (global) 1.39×10⁻⁵ (local) |
| | SRI-8963 | 241 | 7 | >50 | 4 | >90 | N/A | 3.09×10⁻⁵ (global) | 1.75×10⁻⁷ (global) 2.53×10⁻⁶ (local) |
| | SRI-0070 | 435 | 3.5 | 54.6 | 4.7 | >100 | 6.13×10⁻⁷ (local) | N/A | 4.66×10⁻⁶ (local) |
| | SRI-0577 | 376 | 10.7 | >100 | 0.7 | 40 | 2.16×10⁻⁶ (local) | N/A | 6.77×10⁻⁸ (local) |

[a] SPR using full-length Nef-SF2. Curve fitting using global or local R$_{max}$ as indicated. Gray font indicates Chi² >> R$_{max}$.
[b] N/A: data not available Table 1

SMALL MOLECULES TARGETING HIV-1 NEF

This application is a divisional of U.S. application Ser. No. 15/042,069, filed Feb. 11, 2016, which claims the benefit of U.S. Provisional Application No. 62/116,861, filed Feb. 16, 2015, which is incorporated by reference herein in its entirety.

ACKNOWLEDGMENT OF GOVERNMENT SUPPORT

This invention was made with government support under grant number AI057083 awarded by the National Institutes of Health. The government has certain rights in the invention.

BACKGROUND

The year 2011 marked the 30th anniversary of the HIV/AIDS pandemic with 25 million AIDS-related deaths worldwide and 33 million people currently infected with the virus. The course of the disease changed dramatically with the advent of antiretroviral drugs, which target HIV-1 enzymes critical to the viral life cycle as well as fusion of the virus with the host cell. While cocktails of these drugs have extended the life expectancy of infected individuals, they do not clear the virus and require life-long administration. Chronic drug therapy, coupled with the remarkable mutational capacity of HIV-1, continues to drive drug resistance. The emergence of multi-drug resistant strains of HIV-1, together with uncertain prospects for an effective vaccine, underscores the urgent need for new antiretrovirals with mechanisms of action complementary to existing agents.

SUMMARY

Disclosed herein is a method of treating HIV in a subject, comprising administering to a subject in need thereof a therapeutically effective amount of a compound having a general Formula 1, or a pharmaceutically acceptable salt or ester thereof:

Formula 1 wherein $R^1$ is selected from H, optionally-substituted aryl, optionally-substituted heteroaryl, or optionally-substituted aliphatic; each $R^2$ is independently selected from H, halogen, cyano, thioether, oxo, optionally-substituted amino, optionally-substituted heteroaryl, optionally-substituted aryl, or optionally-substituted aliphatic; a is 3 to 7; and the ring designates a heterocyclic or heteroaryl structure.

Also disclosed herein is a method of treating an HIV-related condition in a subject comprising administering to a subject in need thereof a therapeutically effective amount of a compound having a general Formula 1, or a pharmaceutically acceptable salt or ester thereof:

Formula 1 wherein $R^1$ is selected from H, optionally-substituted aryl, optionally-substituted heteroaryl, or optionally-substituted aliphatic; each $R^2$ is independently selected from H, halogen, cyano, thioether, oxo, optionally-substituted amino, optionally-substituted heteroaryl, optionally-substituted aryl, or optionally-substituted aliphatic; a is 3 to 7; and the ring designates a heterocyclic or heteroaryl structure.

Further disclosed herein is a method for inhibiting a biological function of Nef, comprising contacting Nef with an effective amount of a compound having a general Formula 1, or a pharmaceutically acceptable salt or ester thereof:

Formula 1 wherein $R^1$ is selected from H, optionally-substituted aryl, optionally-substituted heteroaryl, or optionally-substituted aliphatic; each $R^2$ is independently selected from H, halogen, cyano, thioether, oxo, optionally-substituted amino, optionally-substituted heteroaryl, optionally-substituted aryl, or optionally-substituted aliphatic; a is 3 to 7; and the ring designates a heterocyclic or heteroaryl structure.

Additionally disclosed herein is a method of treating a Nef-mediated disease in a subject, comprising administering to a subject in need thereof a therapeutically effective amount of a compound having a general Formula 1, or a pharmaceutically acceptable salt or ester thereof:

Formula 1 wherein $R^1$ is selected from H, optionally-substituted aryl, optionally-substituted heteroaryl, or optionally-substituted aliphatic; each $R^2$ is independently selected from H, halogen, cyano, thioether, oxo, optionally-substituted amino, optionally-substituted heteroaryl, optionally-substituted aryl, or optionally-substituted aliphatic; a is 3 to 7; and the ring designates a heterocyclic or heteroaryl structure.

Also disclosed herein is a method of inhibiting an activity of a Nef-dependent kinase comprising contacting the Nef-dependent kinase with an effective amount of a compound having a general Formula 1, or a pharmaceutically acceptable salt or ester thereof:

Formula 1 wherein R[1] is selected from H, optionally-substituted aryl, optionally-substituted heteroaryl, or optionally-substituted aliphatic; each R[2] is independently selected from H, halogen, cyano, thioether, oxo, optionally-substituted amino, optionally-substituted heteroaryl, optionally-substituted aryl, or optionally-substituted aliphatic; a is 3 to 7; and the ring designates a heterocyclic or heteroaryl structure.

Further disclosed herein is a pharmaceutical composition, comprising a compound having a Formula 1, or a pharmaceutically acceptable salt or ester thereof:

Formula 1 wherein R[1] is selected from H, optionally-substituted aryl, optionally-substituted heteroaryl, or optionally-substituted aliphatic; each R[2] is independently selected from H, halogen, cyano, thioether, oxo, optionally-substituted amino, optionally-substituted heteroaryl, optionally-substituted aryl, or optionally-substituted aliphatic; a is 3 to 7; and the ring designates a heterocyclic or heteroaryl structure; and
at least one pharmaceutically acceptable additive.

The foregoing will become more apparent from the following detailed description, which proceeds with reference to the accompanying FIGURES.

BRIEF DESCRIPTION OF THE DRAWINGS

FIG. 1 depicts Table 1 showing assay results for four compounds as disclosed herein.

DETAILED DESCRIPTION

Terms

Unless otherwise explained, all technical and scientific terms used herein have the same meaning as commonly understood by one of ordinary skill in the art to which a disclosed technology belongs. The singular terms "a," "an," and "the" include plural referents unless context clearly indicates otherwise. Similarly, the word "or" is intended to include "and" unless the context clearly indicates otherwise. "Comprising" means "including." Hence "comprising A or B" means "including A" or "including B" or "including A and B."

All publications, patent applications, patents, and other references mentioned herein are incorporated by reference in their entirety for all purposes. In case of conflict, the present specification, including explanations of terms, will control.

Although methods and materials similar or equivalent to those described herein can be used to practice or test the disclosed technology, suitable methods and materials are described below. The materials, methods, and examples are illustrative only and not intended to be limiting.

In order to facilitate review of the various embodiments of the disclosure, the following explanations of specific terms are provided:

Aliphatic: A substantially hydrocarbon-based compound, or a radical thereof (e.g., $C_6H_{13}$, for a hexane radical), including alkanes, alkenes, alkynes, including cyclic versions thereof, and further including straight- and branched-chain arrangements, and all stereo and position isomers as well.

Alkyl: A saturated aliphatic group comprising carbon and hydrogen atoms, typically having from 1 to about 10 carbon atoms, more typically from 1 to about 6 carbon atoms. This term includes straight chain alkyl groups as well as branched alkyl groups. Exemplary alkyl groups include methyl, ethyl, n-propyl, i-propyl, n-butyl, i-butyl, sec-butyl, t-butyl, n-pentyl, neopentyl, and n-hexyl. This term includes substituted alkyl groups, which are alkyl groups having from 1 to 5 hydrogen atoms being replaced with any substituent recited herein.

Alkoxy: This term includes alkyl groups comprising an oxygen atom, such as —OMe, -OEt, and the like. This term also includes oxygen-containing substituted alkyl groups, which are alkyl groups having from 1 to 5 hydrogen atoms being replaced with any substituent recited herein.

Amide: This term refers to the group —C(O)NH$_2$. This term also includes substituted amide groups having a formula —C(O)NR[7]R[8] wherein R[7] and R[8] may be selected from hydrogen, aliphatic, heteroaliphatic, aryl, and heteroaryl.

Amino: This term refers to the group —NH$_2$. This term also includes substituted amino groups having a formula NR[7]R[8] wherein R[7] and R[8] may be selected from hydrogen, aliphatic, heteroaliphatic, aryl, and heteroaryl.

Aryl: An aromatic cyclic group comprising from 6 to about 14 carbon atoms. The carbon atoms may comprise a single ring, or one or more fused rings wherein at least one of the fused rings is aromatic. Exemplary embodiments are phenyl, naphthyl or anthryl. This term includes aryl groups having 1 to 5 hydrogen atoms replaced with any substituent provided herein.

Carboxyl: This term refers to the group —C(O)OH, or a salt thereof.

The term "co-administration" or "co-administering" refers to administration of a compound disclosed herein with at least one other therapeutic or diagnostic agent within the same general time period, and does not require administration at the same exact moment in time (although co-administration is inclusive of administering at the same exact moment in time). Thus, co-administration may be on the same day or on different days, or in the same week or in different weeks. In certain embodiments, a plurality of therapeutic and/or diagnostic agents may be co-administered by encapsulating the agents within the dendrimeric platform disclosed herein and/or by covalently conjugating the agents to the surface of the dendrimeric platform.

Cyano: This term refers to the group —CN.

Cycloalkyl: This term refers to a cyclic alkyl group comprising from 3 to about 10 carbon atoms having one or more rings.

Ester: This term refers to a carboxyl group substituted with an alkyl group, such as methyl, ethyl, propyl, and the like. Exemplary embodiments are —C(O)OMe and —C(O)OEt.

Guanidino: This term refers to the group —NHC(=NH)NH$_2$ and also encompasses substituted guanidino groups having a formula —NHC(=NH)NR[7]R[8] wherein R[7] and R[8] may be selected from hydrogen, aliphatic, heteroaliphatic, aryl, and heteroaryl.

Halogen (or Halo): This term includes fluoro, iodo, bromo, and chloro.

Heteroaliphatic: This term refers to an aliphatic group comprising at least one heteroatom selected from oxygen, sulfur, and nitrogen.

Heteroaryl: This term refers to an aromatic group comprising from 5 to about 15 atoms in the ring, wherein at least one of those atoms is a heteroatom selected from oxygen, nitrogen, or sulfur. This term includes single rings and fused ring systems. This term also includes substituted heteroaryl groups comprising from 1 to about 5 substituents selected from the groups provided herein.

Heterocyclic: This term refers to a saturated or unsaturated cyclic group comprising from 1 to about 10 carbon atoms and at least one heteroatom selected from oxygen, nitrogen, or sulfur. This term also includes substituted heterocyclic groups comprising from 1 to about 5 substituents attached to at least one carbon atom of the ring, wherein the substituent may be selected from any substituent disclosed herein.

Hydroxyl: This term refers to the group —OH.

Nitro: This term refers to the group —NO$_2$.

Prodrug: This term refers, typically, to a pharmacologically inactive derivative of the disclosed compound that may be converted to an active form of the disclosed compound by removal of a progroup. The compounds disclosed herein may exist as a prodrug, wherein one or more of the functional groups on the compound is converted into a progroup. In particular disclosed embodiments, the compound may comprise a hydroxyl group, an amine group, a thiol group, or a carboxyl group that is converted into a progroup. Solely by way of example, a hydroxyl group may be functionalized to provide a sulfonate (e.g., mesylate, triflate, tosylate, and the like), an ester group, or an alkyl group. Solely by way of example, an amine may be functionalized to provide an amide group or an ester group. Solely by way of example, a carboxyl group may be functionalized to provide an ester group or an amide group.

Progroup: This term refers to a protecting group that may be attached to a functional group present on the disclosed compound(s) via one or more bonds that may be cleaved under particular conditions, such as acidic conditions, hydrolysis conditions, or enzymatic cleavage conditions.

Pyridyl: This term refers to the aromatic group —C$_5$H$_4$N. As disclosed herein, this group may be substituted with one or more substituents recited herein.

"Substituted" or "substitution" refers to replacement of a hydrogen atom of a molecule or an R-group with one or more additional R-groups. Unless otherwise defined, the term "optionally-substituted" or "optional substituent" as used herein refers to a group which may or may not be further substituted with 1, 2, 3, 4 or more groups, preferably 1, 2 or 3, more preferably 1 or 2 groups. The substituents may be selected, for example, from C$_{1-6}$alkyl, C$_{2-6}$alkenyl, C$_{2-6}$alkynyl, C$_{3-8}$cycloalkyl, hydroxyl, oxo, C$_{1-6}$alkoxy, aryloxy, C$_{1-6}$alkoxyaryl, halo, C$_{1-6}$alkylhalo (such as CF$_3$ and CHF$_2$), C$_{1-6}$alkoxyhalo (such as OCF$_3$ and OCHF$_2$), carboxyl, esters, cyano, nitro, amino, substituted amino, disubstituted amino, acyl, ketones, amides, aminoacyl, substituted amides, disubstituted amides, thiol, alkylthio, thioxo, sulfates, sulfonates, sulfinyl, substituted sulfinyl, sulfonyl, substituted sulfonyl, sulfonylamides, substituted sulfonamides, disubstituted sulfonamides, aryl, arC$_{1-6}$alkyl, heterocyclyl and heteroaryl wherein each alkyl, alkenyl, alkynyl, cycloalkyl, aryl and heterocyclyl and groups containing them may be further optionally substituted. Optional substituents in the case N-heterocycles may also include but are not limited to C$_{1-6}$alkyl i.e. N—C$_{1-3}$alkyl, more preferably methyl particularly N-methyl.

A "therapeutically effective amount" refers to a quantity of a specified agent sufficient to achieve a desired effect in a subject being treated with that agent. Ideally, a therapeutically effective amount of an agent is an amount sufficient to inhibit or treat the disease or condition without causing a substantial cytotoxic effect in the subject. The therapeutically effective amount of an agent will be dependent on the subject being treated, the severity of the affliction, and the manner of administration of the therapeutic composition.

Thio (or Thiol): This term refers to the group —SH.

Thioether: This term refers to a thio group substituted with an aliphatic group, such as an alkyl group, as defined herein. This term also includes substituted thioether groups comprising substituted alkyl groups, as defined herein.

"Treatment" refers to a therapeutic intervention that ameliorates a sign or symptom of a disease or pathological condition after it has begun to develop, or administering a compound or composition to a subject who does not exhibit signs of a disease or exhibits only early signs for the purpose of decreasing the risk of developing a pathology or condition, or diminishing the severity of a pathology or condition. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" refers to inhibiting the full development of a disease, for example, in a subject who is at risk for a disease such as diabetes. "Preventing" a disease or condition refers to prophylactic administering a composition to a subject who does not exhibit signs of a disease or exhibits only early signs for the purpose of decreasing the risk of developing a pathology or condition, or diminishing the severity of a pathology or condition.

The terms "pharmaceutically acceptable salt or ester" refers to salts or esters prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977).

"Pharmaceutically acceptable esters" includes those derived from compounds described herein that are modified to include a carboxyl group. An in vivo hydrolysable ester is an ester, which is hydrolysed in the human or animal body to produce the parent acid or alcohol. Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example benzyl), aryloxyalkyl (for example, phenoxymethyl), aryl (for example, phenyl, optionally substituted by, for example, halogen, $C_{1-4}$ alkyl, or $C_{1-4}$ alkoxy) or amino); sulphonate esters, such as alkyl- or aralkylsulphonyl (for example, methanesulphonyl); or amino acid esters (for example, L-valyl or L-isoleucyl). A "pharmaceutically acceptable ester" also includes inorganic esters such as mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group, optionally substituted as shown in the definition of carbocycylyl above. Pharmaceutically acceptable esters thus include $C_1$-$C_{22}$ fatty acid esters, such as acetyl, t-butyl or long chain straight or branched unsaturated or omega-6 monounsaturated fatty acids such as palmoyl, stearoyl and the like. Alternative aryl or heteroaryl esters include benzoyl, pyridylmethyloyl and the like any of which may be substituted, as defined in carbocyclyl above. Additional pharmaceutically acceptable esters include aliphatic L-amino acid esters such as leucyl, isoleucyl and especially valyl.

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned hereinabove are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "addition salt" as used hereinabove also comprises the solvates which the compounds described herein are able to form. Such solvates are for example hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

HIV-Nef Function Antagonist

In addition to viral enzymes and structural proteins, the HIV-1 genome encodes a unique set of accessory factors (Vpr, Vpu, Vif, and Nef) that are essential for viral pathogenesis and represent underexplored targets for new anti-retroviral drug discovery. HIV-1 Nef is particularly attractive in this regard, as it enhances HIV infectivity, promotes viral replication, and enables immune escape of HIV-infected cells. Nef lacks known biochemical activity, functioning instead through interactions with a myriad of host cell proteins. These interactions provide a molecular basis for many Nef functions, including downregulation of viral (CD4/CXCR4/CCR5) and immune (MHC-I) receptors from the host cell surface. Nef-mediated receptor internalization is believed to prevent superinfection and enhance viral release, while MHC-I downregulation promotes evasion of immune surveillance by the host.

A critical role for Nef in HIV disease has also been established in animal models as well as AIDS patients. Nef is required for the high-titer replication of both HIV and SIV in vivo, and is essential for the development of AIDS-like disease in non-human primates. Furthermore, targeted expression of Nef in the T-cells and macrophages of transgenic mice induces a severe AIDS-like syndrome, strongly supporting an essential role for this single viral protein in HIV-1 pathogenesis. The phenotype of these Nef-transgenic mice recapitulates many aspects of human AIDS, including profound immunodeficiency, loss of CD4+ T cells, thymic atrophy, persistent T-cell activation, as well as kidney, spleen, and lung pathology. In contrast, HIV strains with defective nef alleles have been isolated from patients with long-term, non-progressive HIV infections. Similarly, CD4+ T-cell depletion and immunosuppression was greatly delayed in a cohort of individuals infected with a Nef-deficient HIV-1 quasispecies, providing strong clinical evidence that Nef is essential for disease progression in humans.

Disclosed herein are embodiments of compounds for treating HIV. In particular disclosed embodiments, the compounds are capable of inhibiting Nef, such as by acting as a HIV-Nef function antagonist. The compounds are small molecule compounds that are capable of inhibiting both HIV-1 infectivity and replication. The compounds may be active against HIV-1 replication supported by Nef alleles representative of all major subtypes of HIV-1. The disclosed compounds are capable of binding to Nef and thereby altering or inhibiting its activity. In particular disclosed embodiments, the compounds may bind electrostatically, via hydrogen bonding, or covalently.

The compounds disclosed herein may be HIV-Nef function antagonists having a general Formula 1, illustrated below, or a pharmaceutically acceptable salt, or ester thereof.

Formula 1 wherein $R^1$ is selected from H, optionally-substituted aryl, optionally-substituted heteroaryl, or optionally-substituted aliphatic; each $R^2$ is independently selected from H, halogen, cyano, thioether, oxo, optionally-substituted amino, optionally-substituted heteroaryl, optionally-substituted aryl, or optionally-substituted aliphatic; a is 3 to 7; and the ring designates a heterocyclic or heteroaryl structure.

In certain embodiments, $R^1$ is H, halogen-substituted phenyl, or alkyl-substituted phenyl.

In certain embodiments, at least one of $R^2$ is not H.

In certain embodiments, a is 3, 4, or 7.

The compounds disclosed herein may be HIV-Nef function antagonists having a general Formula 1a, illustrated below, or a pharmaceutically acceptable salt, or ester thereof.

Formula 1a wherein $R^3$ is H; each of $R^4$-$R^7$ is independently selected from H, halogen, cyano, thio ether optionally-substituted heteroaryl or optionally-substituted amino; and A is N and B is C or A is C and B is N; provided that when A is N then $R^6$ is not present or when B is N then $R^7$ is not present.

In certain embodiments, $R^4$ is halogen or cyano.

In certain embodiments, $R^5$ is optionally-substituted amino or optionally-substituted heteroaryl.

In certain embodiments, B is N, A is C, and $R^6$ is H.

In certain embodiments, B is C, A is N, and $R^7$ is thioether.

The compounds disclosed herein may be HIV-Nef function antagonists having a general Formula 1b, illustrated below, or a pharmaceutically acceptable salt, or ester thereof.

Figure 1B:
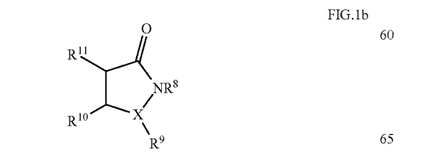

FIG.1b wherein $R^8$ is H or optionally-substituted aryl; $R^9$ is optionally-substituted aryl; each of $R^{10}$ or $R^{11}$ is independently selected from H, optionally-substituted aliphatic, oxo, or $R^{10}$ and $R^{11}$ together form a heteroaryl ring; and X is S or N; provided that if X is S then $R^9$ is not present.

In certain embodiments, $R^8$ is alkyl-substituted phenyl or halo-substituted phenyl.

In certain embodiments, $R^9$ is alkyl-substituted phenyl or halo-substituted phenyl.

In certain embodiments, $R^{10}$ is oxo.

In certain embodiments, $R^{11}$ is substituted alkenyl.

The compounds disclosed herein may be HIV-Nef function antagonists having a general Formula 1c, illustrated below, or a pharmaceutically acceptable salt, or ester thereof.

Figure 1C:
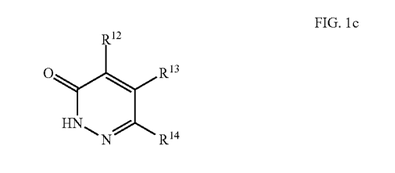

FIG. 1c wherein $R^{12}$ is H, halo, halo-substituted alkyl; $R^{13}$ is substituted amino; and $R^{14}$ is H.

The compounds disclosed herein may be HIV-Nef function antagonists having a general Formula 1d, illustrated below, or a pharmaceutically acceptable salt, or ester thereof.

Figure 1D:
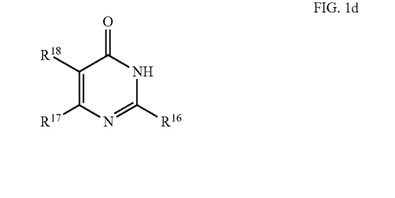

FIG. 1d wherein $R^{16}$ is substituted thioether; $R^{17}$ is heteroaryl; and $R^{18}$ is cyano.

The compounds disclosed herein may be HIV-Nef function antagonists having a general Formula 1e, illustrated below, or a pharmaceutically acceptable salt, or ester thereof.

Figure 1E:
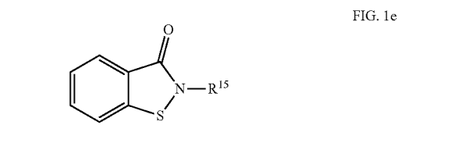

FIG. 1e wherein $R^{15}$ is alkyl-substituted phenyl.

The compounds disclosed herein may be HIV-Nef function antagonists having a general Formula 1f, illustrated below, or a pharmaceutically acceptable salt, or ester thereof.

Figure 1F:
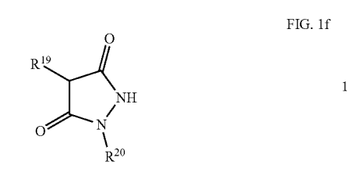

FIG. 1f wherein $R^{19}$ is substituted alkenyl; and $R^{20}$ is halo-substituted phenyl.

Illustrative compounds are shown below:

The compound disclosed herein also may exist as a pharmaceutically acceptable salt. In particular disclosed embodiments, the compound may be a salt derived from a variety of counter ions, both organic or inorganic, selected from, but not limited to ammonium, calcium, magnesium, potassium, sodium, and tetraalkylammonium. In particular disclosed embodiments, the compound may be a pharmaceutically acceptable salt selected from a hydrochloride, hydrobromide, tartrate, mesylate, acetate, and the like. The pharmaceutically acceptable salts disclosed herein may either be formed by replacing an acidic proton of the parent compound with a metal ion, or when the acidic proton of the parent compound coordinates with an organic base (e.g., an amine-containing base, such as dimethylamine, di- or triethylamine, ammonia, and the like).

Certain embodiments of the compound disclosed herein exhibit sufficient aqueous solubility necessary for in vitro and/or in vivo applications. Also, embodiments of the disclosed compound exhibit pharmacologically significant early-stage metabolic profiles. Preferred compounds are those that are potent, but are suitable for administering at low dosages.

The compound disclosed herein may be administered alone or in combination with one or more other components. In particular disclosed embodiments, the compound may be administered with one or more pharmacologically active agents. The disclosed compound may function additively or synergistically with the one or more pharmacologically active agents. In particular disclosed embodiments, the compound may be used in combination with one or more of these pharmacologically active agents in order to lower the effective dose needed for treatment. The ability to reduce effective doses of the pharmacologically active agent may aid in reducing drug resistance and/or cumulative toxicity. In particular disclosed embodiments, the compound and the pharmacologically active agent are administered sequentially. In other disclosed embodiments, the compound and the pharmacologically active agent may be administered simultaneously in the same or separate mode of administration.

Examples of the pharmacologically active agent include, but are not limited to, antiretroviral agents. In particular disclosed embodiments, the antiretroviral agent is selected from an entry inhibitor, a CCR5 receptor antagonist, a nucleoside reverse transcriptase inhibitor, a non-nucleoside reverse transcriptase inhibitor, a protease inhibitor, an integrase inhibitor, a maturation inhibitor, or combinations thereof. Exemplary antiretroviral agents include, but are not limited to, maraviroc, enfuvirtide, aplaviroc, vicriviroc, zidovudine, didanosine, zalcitabine, stavudine, lamivudine, abacavir, emtricitabine, entecavir, apricitabine, tenofovir, adefovir, efavirenz, nevirapine, delavirdine, etravirine, rilpivirine, saquinavir, ritonavir, indinavir, nelfinavir, amprenavir, lopinavir atazanavir fosamprenavir tipranavir darunavir, MK-2048, elvitegravir, bevirimat, MPC-9055, or combinations thereof.

The compound may also be administered with one or more conventional non-toxic pharmaceutically acceptable carriers, and excipients appropriate for each route of administration. Non-limiting examples of pharmaceutically acceptable carriers include sterile solutions, tablets, capsules, buffers, saline, and the like. Non-limiting examples of excipients include anti-adherents (e.g., magnesium stearate), binders (e.g., saccharides, such as sucrose, lactose, starches, cellulose, xylitol, sorbitol, and maltitol; gelatin; and synthetic polymers), coatings (e.g., hydroxypropyl methylcellulose, gelatin, and the like), disintegrants (e.g., potato starch, sodium starch glycolate, and the like), fillers (e.g., lactose, sucrose, glucose mannitol, sorbitol, calcium carbonate, and magnesium stearate), flavors (e.g., mint, cherry, anise, vanilla, and the like), colors (e.g., any color that improves the appearance of a formulation of the compound), lubricants (talc, silica, fat, stearic acid, and the like), glidants (e.g., magnesium carbonate, talc, and the like), sorbents (e.g., fatty acids, waxes, plastics, and plant fibers), preservatives (e.g., antioxidants, cysteine, methionine, citric acid, and the like), sweeteners (e.g., corn syrup, sugar, and the like), or combinations thereof.

In particular disclosed embodiments, the compound may be administered using methods known to those of ordinary skill in the art as being suitable for exposing a patient to sufficient dosages of the disclosed compound. Certain modes of administration are contemplated by the present disclosure, including, but not limited to oral (e.g., capsule, tablet, lozenge, syrup, or powder); intramuscular, intraperitoneal, intravenous, intracisternal injection or infusion (e.g., sterile suspensions, solutions, or emulsions); subcutaneous injection (e.g., sterile suspensions, solutions, or emulsions); implant; nasal inhalation (e.g., aerosol spray administered via inhaler, liquid nebulizer, sprayer, or thermal vaporizer); vaginal (e.g., solution, suppository, or ointment); rectal (e.g., solution, suppository, or ointment); or topically (e.g., gel, ointment, cream, aerosol, etc.).

In particular disclosed embodiments, the compound is administered to a patient medically diagnosed with HIV or exhibiting symptoms associated with HIV. The patient may be identified using any method known to those of ordinary skill in the art, such as rapid or standard enzyme immunoassay screening, a confirmatory test, such as a Western blot, or an HIV antigen/antibody test. In other disclosed embodiments, the patient may be selected based on physical symptoms, such fever, fatigue, rash, headache, swollen lymph nodes, and sore throat. The compound may also be administered to a patient prophylactically or post-exposure prophylactically. Solely by way of example, the patient may be administered the compound after occupational exposure, non-occupational exposure, or if the patient anticipates exposure.

Method of Using the HIV-Nef Function Antagonist

The present disclosure also concerns embodiments of a method of using the disclosed compound. In particular disclosed embodiments, the method concerns inhibiting a biological function of Nef, the method comprising contacting Nef with an effective amount of a compound as disclosed herein. In particular disclosed embodiments, the method may concern using a compound having any one of Formulas 1-1f, which are disclosed herein. The biological function may be selected from HIV infectivity, HIV replication, AIDS progression, or combinations thereof.

Also disclosed is a method of inhibiting an activity of a Nef-dependent kinase comprising contacting the Nef-dependent kinase with an effective amount of a compound as disclosed herein. In particular disclosed embodiments, the Nef-dependent kinase may be a Src kinase, such as Hck, or a Tec family kinase, such as Itk.

Particular embodiments concern a method of treating a Nef-mediated disease, comprising administering to a subject a therapeutically effective amount of a compound as disclosed herein. In other embodiments, the method may concern treating an HIV-related condition, the method comprising administering to a subject a therapeutically effective amount of a compound as disclosed herein. The HIV-related condition may be selected from HIV replication, HIV-associated CD4+ T-cell loss and immunodeficiency, HIV-induced infection, Kaposi's sarcoma, HIV-associated nephropathy, AIDS dementia complex, and combinations thereof.

Embodiments of the disclosed method may be used when the subject is suffering from the HIV-related condition, or the method may be practiced prophylactically or post-exposure prophylactically.

The effective amount used in the disclosed method may be that which is best suited for treating the subject. The effective amount may range from greater than zero to about 1000 mg/kg/day. In particular disclosed embodiments, the effective amount ranges from 1 mg/kg/day to about 100 mg/kg/day. The subject of the disclosed method may be human or an animal and the method may be performed in vitro or in vivo.

The compound disclosed herein may be used in therapy for a Nef-dependent disorder. As disclosed herein, the compound may be used to treat and/or inhibit a biological pathway that is activated by Nef. Such pathways include, but are not limited to, pathways involving a Src-family kinase, such as Hck. In particular disclosed embodiments, the compound may be used to treat or inhibit Nef-dependent HIV-1 replication both in vitro and in vivo. The disclosed compound also may be used to treat or inhibit Nef-dependent HIV-1 infectivity. The disclosed compound therefore may be used to treat HIV. In other disclosed embodiments, the compound may be used to treat or inhibit SIV infectivity or replication.

Particular disclosed embodiments of the compound disclosed herein are potent and selective inhibitors of Nef-dependent Hck activity and therefore may be used in in vitro, in vivo, and ex vivo contexts to regulate or inhibit this activity, prevent any Nef-dependent HIV-1 replication, and downregulate MHC-1, as well as the biological responses that result from such activity. In particular disclosed embodiments, the compound may be used to inhibit HIV-1 infectivity and replication in cell types selected from, but not limited to, U87MG astroglioma cells, CEM-T4 lymphoblasts, TZM-bl reporter cell line, and CEM-174. Particular disclosed embodiments of the compound disclosed herein may be used to inhibit Nef-dependent HIV replication in the submicromolar range. Embodiments of the disclosed compound may exhibit $IC_{50}$ values for Nef-induced Hck activation in vitro of less than about 3.0 μM; more typically less that about 2.5 μM; even more typically less than about 2.0 μM.

In particular disclosed embodiments, the compound is capable of preventing and/or inhibiting Nef-dependent enhancement of HIV-1 infectivity and replication. The compound is not limited to being active against any particular Nef allele. For instance, embodiments of the disclosed compound are active against a variety of Nef alleles, particularly those that comprise the HIV-1 M-group clades. Exemplary embodiments of the compound may inhibit the replication of various HIV-1 Nef chimeras with an $IC_{50}$ value of 100 nM to about 400 nM; more typically from about 200 nM to about 350 nM; even more typically from about 250 nM to about 300 nM.

Several illustrative embodiments are described below in the following numbered clauses:

1. A method of treating HIV in a subject, comprising administering to a subject in need thereof a therapeutically effective amount of a compound having a general Formula 1, or a pharmaceutically acceptable salt or ester thereof:

Formula 1 wherein $R^1$ is selected from H, optionally-substituted aryl, optionally-substituted heteroaryl, or optionally-substituted aliphatic; each $R^2$ is independently selected from H, halogen, cyano, thioether, oxo, optionally-substituted amino, optionally-substituted heteroaryl, optionally-substituted aryl, or optionally-substituted aliphatic; a is 3 to 7; and the ring designates a heterocyclic or heteroaryl structure.

2. A method of treating an HIV-related condition in a subject comprising administering to a subject in need thereof a therapeutically effective amount of a compound having a general Formula 1, or a pharmaceutically acceptable salt or ester thereof:

Formula 1 wherein $R^1$ is selected from H, optionally-substituted aryl, optionally-substituted heteroaryl, or optionally-substituted aliphatic; each $R^2$ is independently selected from H, halogen, cyano, thioether, oxo, optionally-substituted amino, optionally-substituted heteroaryl, optionally-substituted aryl, or optionally-substituted aliphatic; a is 3 to 7; and the ring designates a heterocyclic or heteroaryl structure.

3. A method for inhibiting a biological function of Nef, comprising contacting Nef with an effective amount of a compound having a general Formula 1, or a pharmaceutically acceptable salt or ester thereof:

Formula 1 wherein $R^1$ is selected from H, optionally-substituted aryl, optionally-substituted heteroaryl, or optionally-substituted aliphatic; each $R^2$ is independently selected from H, halogen, cyano, thioether, oxo, optionally-substituted amino, optionally-substituted heteroaryl, optionally-substituted aryl, or optionally-substituted aliphatic; a is 3 to 7; and the ring designates a heterocyclic or heteroaryl structure.

4. A method of treating a Nef-mediated disease in a subject, comprising administering to a subject in need thereof a therapeutically effective amount of a compound having a general Formula 1, or a pharmaceutically acceptable salt or ester thereof:

Formula 1 wherein $R^1$ is selected from H, optionally-substituted aryl, optionally-substituted heteroaryl, or optionally-substituted aliphatic; each $R^2$ is independently selected from H, halogen, cyano, thioether, oxo, optionally-substituted amino, optionally-substituted heteroaryl, optionally-substituted aryl, or optionally-substituted aliphatic; a is 3 to 7; and the ring designates a heterocyclic or heteroaryl structure.

5. A method of inhibiting an activity of a Nef-dependent kinase comprising contacting the Nef-dependent kinase with an effective amount of a compound having a general Formula 1, or a pharmaceutically acceptable salt or ester thereof:

Formula 1 wherein $R^1$ is selected from H, optionally-substituted aryl, optionally-substituted heteroaryl, or optionally-substituted aliphatic; each $R^2$ is independently selected from H, halogen, cyano, thioether, oxo, optionally-substituted amino, optionally-substituted heteroaryl, optionally-substituted aryl, or optionally-substituted aliphatic; a is 3 to 7; and the ring designates a heterocyclic or heteroaryl structure.

6. The method according to clause 2 wherein the HIV-related condition is selected from HIV replication, HIV-associated CD4+ T-cell loss and immunodeficiency, HIV-induced infection, Kaposi's sarcoma, HIV-associated nephropathy, AIDS dementia complex, or combinations thereof.

7. The method of clause 1 or clause 2 wherein the subject is administered the compound prophylactically.

8. The method of clause 1 or clause 2 wherein the subject is administered the compound post-exposure prophylactically.

9. The method of any one of clauses 1 to 8 wherein the compound is administered as a pharmaceutical composition.

10. The method of clause 9 wherein the pharmaceutical composition comprises the compound and a pharmaceutically acceptable carrier.

11. The method of clause 9 or clause 10 wherein the pharmaceutical composition further comprises at least one antiretroviral drug.

12. The method of clause 11 wherein the at least one antiretroviral drug is selected from an entry inhibitor, a CCR5 receptor antagonist, a nucleoside reverse transcriptase inhibitor, a non-nucleoside reverse transcriptase inhibitor, a protease inhibitor, an integrase inhibitor, a maturation inhibitor, or a combination thereof.

13. The method of clause 11 or clause 12 wherein the at least one antiretroviral drug is selected from maraviroc, enfuvirtide, aplaviroc, vicriviroc, zidovudine, didanosine, zalcitabine, stavudine, lamivudine, abacavir, emtricitabine, entecavir, apricitabine, tenofovir, adefovir, efavirenz, nevirapine, delavirdine, etravirine, rilpivirine, saquinavir, ritonavir, indinavir, nelfinavir, amprenavir, lopinavir atazanavir fosamprenavir tipranavir darunavir, MK-2048, elvitegravir, bevirimat, MPC-9055, or a combination thereof.

14. The method of any one of clauses 1 to 13 wherein $R^1$ is H, halogen-substituted phenyl, or alkyl-substituted phenyl.

15. The method of any one of clauses 1 to 14 wherein at least one of $R^2$ is not H.

16. The method of any one of clauses 1 to 15 wherein a is 3, 4, or 7.

17. The method of any of clauses 1 to 13 wherein the compound has a general Formula 1a, or a pharmaceutically acceptable salt or ester thereof:

Formula 1a wherein $R^3$ is H; each of $R^4$-$R^7$ is independently selected from H, halogen, cyano, thio ether optionally-substituted heteroaryl or optionally-substituted amino; and A is N and B is C or A is C and B is N; provided that when A is N then $R^6$ is not present or when B is N then $R^7$ is not present.

18. The method of clause 17 wherein $R^4$ is halogen or cyano.

19. The method of clause 17 or 18 wherein $R^5$ is optionally-substituted amino or optionally-substituted heteroaryl.

20. The method of any one of clauses 17 to 19 wherein B is N, A is C, and $R^6$ is H.

21. The method of any one of clauses 17 to 19 wherein B is C, A is N, and $R^7$ is thioether.

22. The method of any of clauses 1 to 13 wherein the compound has a general Formula 1b or a pharmaceutically acceptable salt or ester thereof:

FIG. 1b wherein $R^8$ is H or optionally-substituted aryl; $R^9$ is optionally-substituted aryl; each of $R^{10}$ or $R^{11}$ is independently selected from H, optionally-substituted aliphatic, oxo, or $R^{10}$ and $R^{11}$ together form a heteroaryl ring; and X is S or N; provided that if X is S then $R^9$ is not present.

23. The method of clause 22 wherein $R^8$ is alkyl-substituted phenyl or halo-substituted phenyl.

24. The method of clause 22 or 23 wherein $R^9$ is alkyl-substituted phenyl or halo-substituted phenyl.

25. The method of any one of clauses 22 to 24 wherein $R^{10}$ is oxo.

26. The method of any one of clauses 22 to 25 wherein $R^{11}$ is substituted alkenyl.

27. The method of any of clauses 1 to 13 wherein the compound has a general Formula 1c, or a pharmaceutically acceptable salt or ester thereof:

FIG. 1c wherein $R^{12}$ is H, halo, halo-substituted alkyl; $R^{13}$ is substituted amino; and $R^{14}$ is H.

28. The method of any of clauses 1 to 13 wherein the compound has a general Formula 1d, or a pharmaceutically acceptable salt or ester thereof:

FIG. 1d wherein $R^{16}$ is substituted thioether; $R^{17}$ is heteroaryl; and $R^{18}$ is cyano.

29. The method of any of clauses 1 to 13 wherein the compound has a general Formula 1e, or a pharmaceutically acceptable salt or ester thereof:

FIG. 1e wherein $R^{15}$ is alkyl-substituted phenyl.

30. The method of any of clauses 1 to 13 wherein the compound has a general Formula 1f, or a pharmaceutically acceptable salt or ester thereof:

FIG. 1f wherein $R^{19}$ is substituted alkenyl; and $R^{20}$ is halo-substituted phenyl.

31. The method of any of clauses 1 to 13, wherein the compound is selected from:

-continued

; or

32. A pharmaceutical composition, comprising a compound having a Formula 1, or a pharmaceutically acceptable salt or ester thereof:

Formula 1 wherein $R^1$ is selected from H, optionally-substituted aryl, optionally-substituted heteroaryl, or optionally-substituted aliphatic; each $R^2$ is independently selected from H, halogen, cyano, thioether, oxo, optionally-substituted amino, optionally-substituted heteroaryl, optionally-substituted aryl, or optionally-substituted aliphatic; a is 3 to 7; and the ring designates a heterocyclic or heteroaryl structure; and at least one pharmaceutically acceptable additive.

33. The pharmaceutical composition of clause 32 further comprising a pharmacologically active agent other than the compound.

34. The pharmaceutical composition of clause 33 wherein the pharmacologically active agent is an antiretroviral drug.

35. The pharmaceutical composition of clause 34 wherein the antiretroviral drug is selected from an entry inhibitor, a CCR5 receptor antagonist, a nucleoside reverse transcriptase inhibitor, a non-nucleoside reverse transcriptase inhibitor, a protease inhibitor, an integrase inhibitor, a maturation inhibitor, or a combination thereof.

36. The pharmaceutical composition of clause 34 or clause 35 wherein the antiretroviral drug is selected from maraviroc, enfuvirtide, aplaviroc, vicriviroc, zidovudine, didanosine, zalcitabine, stavudine, lamivudine, abacavir, emtricitabine, entecavir, apricitabine, tenofovir, adefovir, efavirenz, nevirapine, delavirdine, etravirine, rilpivirine, saquinavir, ritonavir, indinavir, nelfinavir, amprenavir, lopinavir atazanavir fosamprenavir tipranavir darunavir, MK-2048, elvitegravir, bevirimat, MPC-9055, or combinations thereof.

37. The pharmaceutical composition of any of clauses 32 to 36 wherein the compound has a general Formula 1a, or a pharmaceutically acceptable salt or ester thereof:

Formula 1a wherein $R^3$ is H; each of $R^4$-$R^7$ is independently selected from H, halogen, cyano, thio ether optionally-substituted heteroaryl or optionally-substituted amino; and A is N and B is C or A is C and B is N; provided that when A is N then $R^6$ is not present or when B is N then $R^7$ is not present.

38. The pharmaceutical composition of any of clauses 32 to 36 wherein the compound has a general Formula 1b or a pharmaceutically acceptable salt or ester thereof:

FIG. 1b wherein $R^8$ is H or optionally-substituted aryl; $R^9$ is optionally-substituted aryl; each of $R^{10}$ or $R^{11}$ is independently selected from H, optionally-substituted aliphatic, oxo, or $R^{10}$ and $R^{11}$ together form a heteroaryl ring; and X is S or N; provided that if X is S then $R^9$ is not present.

39. The pharmaceutical composition of any of clauses 32 to 36 wherein the compound has a general Formula 1c, or a pharmaceutically acceptable salt or ester thereof:

FIG. 1c wherein $R^{12}$ is H, halo, halo-substituted alkyl; $R^{13}$ is substituted amino; and $R^{14}$ is H.

40. The pharmaceutical composition of any of clauses 32 to 36 wherein the compound has a general Formula 1d, or a pharmaceutically acceptable salt or ester thereof:

FIG. 1d wherein $R^{16}$ is substituted thioether; $R^{17}$ is heteroaryl; and $R^{18}$ is cyano.

41. The pharmaceutical composition of any of clauses 32 to 36 wherein the compound has a general Formula 1e, or a pharmaceutically acceptable salt or ester thereof:

FIG. 1e wherein $R^{15}$ is alkyl-substituted phenyl.

42. The pharmaceutical composition of any of clauses 32 to 36 wherein the compound has a general Formula 1f, or a pharmaceutically acceptable salt or ester thereof:

FIG. 1f wherein $R^{19}$ is substituted alkenyl; and $R^{20}$ is halo-substituted phenyl.

43. The pharmaceutical composition of any of clauses 32 to 36 wherein the compound is selected from:

Examples

Table 1. Identification of Diverse Chemical Scaffolds Targeting HIV-1 Nef by HTS with the Nef-Hck Assay.

A diverse collection of 720,000 discrete chemical compounds was screened using the FRET-based Nef-Hck in vitro kinase assay as described in detail in Emert-Sedlak, L. A., P. Narute, S. T. Shu, J. A. Poe, H. Shi, N. Yanamala, J. J. Alvarado, J. S. Lazo, J. I. Yeh, P. A. Johnston, and T. E. Smithgall. 2013. Effector Kinase Coupling Enables High-Throughput Screens for Direct HIV-1 Nef Antagonists with Antiretroviral Activity. Chem. Biol. 20:82-91. PMC3559019, which is incorporated by reference herein in its entirety. Hit compounds from the primary screen were then re-screened in concentration-response experiments against the Nef-Hck complex vs. Hck alone, resulting in the identification of 91 compounds demonstrating at least a 10-fold preference for the Nef-Hck complex and an IC50 value for the complex of at least 10 µM. All 91 compounds were then evaluated for antiretroviral activity in primary human monocyte-derived macrophages (MDMs) infected with the M-tropic HIV strain, Ba-L, where HIV-1 Nef enhances viral replication. These experiments identified four unique scaffolds (shown) with antiretroviral activity in the 0.04 to 5 µM range without appreciable toxicity. Each of these compounds was then evaluated for direct binding to recombinant purified HIV-1 Nef using surface plasmon resonance as described in Emert-Sedlak et al. Each of the compounds demonstrated concentration-dependent, saturable binding to Nef. Each SPR data set was fit using three different models and the resulting Kd values are shown. These included 1:1 Langmuir fitting, which gave rise to the kinetic Kd shown; steady state Kd values, based on the Rmax observed at each inhibitor concentration; and a two-state, induced fit model. The general screening and assay methods are also described in WO 2014/074628.

In view of the many possible embodiments to which the principles of the disclosed invention may be applied, it should be recognized that the illustrated embodiments are only preferred examples of the invention and should not be taken as limiting the scope of the invention.

What is claimed is:

1. A method of treating HIV in a subject, comprising administering to a subject in need thereof a therapeutically effective amount of a compound of Formula 1e, or a pharmaceutically acceptable salt or ester thereof:

Formula 1e wherein $R^{15}$ is alkyl-substituted phenyl or halogen-substituted phenyl, and wherein the HIV is Nef-dependent HIV-1.

2. A method of treating an HIV-related condition in a subject in need thereof a therapeutically effective amount of a compound of Formula 1e, or a pharmaceutically acceptable salt or ester thereof:

Formula 1e wherein $R^{15}$ is alkyl-substituted phenyl or halogen-substituted phenyl, and wherein the HIV-related condition is HIV replication, HIV-associated CD4+ T-cell loss and immunodeficiency, HIV-induced infection, Kaposi's sarcoma, HIV-associated nephropathy, AIDS dementia complex, or a combination thereof.

3. The method of claim 1, wherein the compound is

4. The method of claim 2, wherein the compound is

5. The method of claim 1, wherein $R^{15}$ is alkyl-substituted phenyl.

6. The method of claim 2, wherein $R^{15}$ is alkyl-substituted phenyl.

7. The method of claim 1, wherein $R^{15}$ is halogen-substituted phenyl.

8. The method of claim 2, wherein $R^{15}$ is halogen-substituted phenyl.

9. A method of treating HIV in a subject, comprising administering to a subject in need thereof a therapeutically effective amount of a compound of Formula 1e, or a pharmaceutically acceptable salt or ester thereof:

Formula 1e wherein $R^{15}$ is alkyl-substituted phenyl or halogen-substituted phenyl, and wherein the method inhibits HIV-1 infectivity and replication in cell types selected from at least one of U87MG astroglioma cells, CEM-T4 lymphoblasts, TZM-bl reporter cell line, and CEM-174.

10. The method of claim 9, wherein the compound is

11. The method of claim 10, wherein $R^{15}$ is alkyl-substituted phenyl.

* * * * *